US012751785B2

(12) United States Patent
Li et al.

(10) Patent No.: US 12,751,785 B2
(45) Date of Patent: Oct. 6, 2026

(54) OPERATING FEEDBACK OF GUIDEWIRE/CATHETER ADVANCEMENT RESISTANCE FOR VASCULAR INTERVENTION ROBOT

(71) Applicant: SHANGHAI OPERATION ROBOT CO., LTD., Shanghai (CN)

(72) Inventors: Meng Li, Shanghai (CN); Kundong Wang, Shanghai (CN); Qingsheng Lu, Shanghai (CN); Daozhi Liu, Shanghai (CN); Yikun Liu, Shanghai (CN); Zhongwei Yu, Shanghai (CN)

(73) Assignee: SHANGHAI OPERATION ROBOT CO., LTD., Shanghai (CN)

( * ) Notice: Subject to any disclaimer, the term of this patent is extended or adjusted under 35 U.S.C. 154(b) by 1113 days.

(21) Appl. No.: 17/794,236

(22) PCT Filed: Apr. 7, 2020

(86) PCT No.: PCT/CN2020/083457
§ 371 (c)(1),
(2) Date: Jul. 20, 2022

(87) PCT Pub. No.: WO2021/147177
PCT Pub. Date: Jul. 29, 2021

(65) Prior Publication Data

US 2023/0070774 A1 Mar. 9, 2023

(30) Foreign Application Priority Data

Jan. 20, 2020 (CN) ........................ 202010067542.6

(51) Int. Cl.
*A61B 34/00* (2016.01)
*A61B 34/30* (2016.01)
(Continued)

(52) U.S. Cl.
CPC .............. *A61B 34/76* (2016.02); *A61B 34/74* (2016.02); *A61B 2034/301* (2016.02); *A61B 34/37* (2016.02); *A61B 2090/065* (2016.02)

(58) Field of Classification Search
None
See application file for complete search history.

(56) References Cited

U.S. PATENT DOCUMENTS

2011/0087238 A1* 4/2011 Wang ..................... B25J 9/1689 606/130
2019/0290102 A1* 9/2019 Sasaki ................ A61B 1/00042

FOREIGN PATENT DOCUMENTS

CN 107184274 A 9/2017
CN 109199588 A * 1/2019 ............ A61B 34/30
(Continued)

OTHER PUBLICATIONS

Machine Translation of CN 109199588 (Year: 2019).*

*Primary Examiner* — James Kish
(74) *Attorney, Agent, or Firm* — Bayramoglu Law Offices LLC

(57) ABSTRACT

An operating handle with feedback of guidewire/catheter advancement resistance for a vascular intervention robot includes a sliding guide rail, a fixing base plate, a connecting rod, an operation rod, a pressure sensing device, a rotary driving device, and a linear motor. The rotary driving device, the sliding guide rail, and a stator of the linear motor are arranged on the fixing base plate. The pressure sensing device and a rotor of the linear motor are connected with the sliding guide rail through a slider and are able to reciprocate along the sliding guide rail. The connecting rod has one end provided with the operation rod and the other end connected with the rotor of the linear motor through a strain gauge. The
(Continued)

connecting rod passes through the pressure sensing device and the rotary driving device in sequence.

7 Claims, 2 Drawing Sheets

(51) Int. Cl.
*A61B 34/37* (2016.01)
*A61B 90/00* (2016.01)

(56) References Cited

FOREIGN PATENT DOCUMENTS

| | | | |
|---|---|---|---|
| KR | 101949018 | B1 | 4/2019 |
| WO | 2009120992 | A2 | 10/2009 |

* cited by examiner

OPERATING FEEDBACK OF GUIDEWIRE/CATHETER ADVANCEMENT RESISTANCE FOR VASCULAR INTERVENTION ROBOT

CROSS REFERENCE TO THE RELATED APPLICATIONS

This application is the national phase entry of International Application No. PCT/CN2020/083457, filed on Apr. 7, 2020, which is based upon and claims priority to Chinese Patent Application No. 202010067542.6, filed on Jan. 20, 2020, the entire contents of which are incorporated herein by reference.

TECHNICAL FIELD

The present disclosure relates to the field of surgical robot operation, and in particular to an operating handle for a vascular intervention robot that relays the feedback of guidewire/catheter advancement resistance.

BACKGROUND

In recent years, cardiovascular and cerebrovascular diseases have gradually become one of the main factors that threaten people's health. Minimally invasive interventional procedures have gradually become one of the main approaches for the treatment of cardiovascular diseases due to its advantages of high precision, fast speed, and small incisions. Vascular interventional procedures are performed with the aid of X-rays, which results in surgeons having long-term exposure to X-rays. To solve this problem, engineers have developed vascular intervention robots to perform minimally invasive interventional procedures on behalf of surgeons. Surgeons remotely operate vascular intervention robots in an X-ray-free environment to complete vascular interventional procedures. Currently, surgical intervention robots are controlled via touchscreens and operating handles. Vascular interventional procedures rely on a surgeon's control and feedback on the guidewire/catheter. Therefore, the operating handle must issue operating commands to the surgical robot, such as advancing/retreating and rotating the guidewire/catheter. The operating handle must also relay the resistance encountered during the advancement of the guidewire/catheter to the surgeon's hand to help the surgeon determine the current state of the guidewire/catheter in the blood vessel. The feedback of the advancement resistance of the guidewire/catheter can enhance the surgeon's sense of surgical presence, improve surgical safety, and reduce the risk of medical malpractice.

In the touchscreen control mode, the virtual keys on the touchscreen are used to control the vascular intervention robot to advance or rotate the guidewire/catheter, which is not based on the actual surgical action of the surgeon.

The Amigo™ Remote Catheter System, developed by Catheter Robotics, utilizes an operating handle similar to an endoscope control handle to control the motion of vascular intervention robot, including the axial and rotational movements of the guidewire/catheter and the bending angle of the catheter tip. The CorPath® system, developed by Corindus Vascular Robotics, uses a joystick to control the catheter/guidewire. These two operating handles are also not based on the actual surgical action of the surgeon.

The University of Western Ontario in Canada has developed an operating handle for a vascular intervention robot based on a real guidewire/catheter system. Since the operations are performed in a way similar to the real guidewire/catheter, the operating handle can completely replicate the surgeon's hand motions during interventional surgery. However, this operating handle still cannot relay the contact force of the guidewire/catheter inside the blood vessel to the surgeon.

Many academic institutions have studied force feedback of guidewires/catheters in endovascular interventional procedures. The Shibaura Institute of Technology in Japan uses a current-controlled electrorheological fluid to feed back the resistance encountered by the guidewire/catheter in the blood vessel. In China, the Harbin Institute of Technology controls the guidewire/catheter through a roller, and the rotational resistance of the roller reflects the resistance produced by the manipulator of the robot. The Tianjin University of Technology has explored the use of a magnetorheological fluid as a force feedback medium. The Shenzhen Institute of Advanced Technology realizes the main-end operation through the force feedback that is implemented by a motor.

The existing operating handle for a vascular intervention robot mainly relies on the controller of the vascular intervention robot to issue motion instructions to the distal vascular intervention robot to control the rotation, push-pull, or compound actions of the catheter/guidewire. Although the relevant schemes and means of a vascular intervention robot are relatively well-developed, the current difficulty lies in its capability to relay the resistance encountered by the guidewire/catheter in the blood vessel to the surgeon. In particular, there is a need for an operating handle that can simulate the surgeon's real operation actions and provide force feedback. Therefore, it is necessary to explore new principles and structures in terms of real-time performance, dynamic performance, and force coupling between rotational and forward-backward translational motions.

However, there is still a lack of operating handles that replicate the operation action of the surgeon in endovascular interventional surgery and relay the movement resistance of the guidewire/catheter in the blood vessel to the surgeon's hand. The existing schemes are in the experimental stage and have the problems of high manufacturing difficulty, high technical requirements, difficult control, and high research, development, and manufacturing costs.

SUMMARY

In order to overcome the defects in the prior art, an objective of the present disclosure is to provide an operating handle that relays the feedback of guidewire/catheter advancement resistance for a vascular intervention robot.

The operating handle that relays the feedback of guidewire/catheter advancement resistance for a vascular intervention robot provided by the present disclosure includes a sliding guide rail, a fixing base plate, a connecting rod, an operation rod, a pressure sensing device, a rotary driving device, and a linear motor.

The rotary driving device, the sliding guide rail, and a stator of the linear motor are arranged on the fixing base plate.

The pressure sensing device and a rotor of the linear motor are connected with the sliding guide rail through a slider and are able to reciprocate along the sliding guide rail.

The connecting rod has one end provided with the operation rod and the other end connected with the rotor of the linear motor through a strain gauge. The connecting rod passes through the pressure sensing device and the rotary driving device in sequence.

Preferably, the pressure sensing device may include a film-type pressure sensor, a first sliding bearing, and a rotary slip ring.

The film-type pressure sensor may be wrapped on a surface of the operation rod.

The first sliding bearing and the rotary slip ring may be arranged on the sliding guide rail.

The film-type pressure sensor may be electrically connected with the rotary slip ring, and the rotary slip ring may be externally connected with a main controller.

Preferably, the operation rod further may include a second sliding bearing fixed to the fixing base plate; the first sliding bearing and the second sliding bearing support the connecting rod.

Preferably, the rotary driving device may include a fixing base, a rotary encoder, a rotary driving piece, and a rotary driving rod.

The rotary encoder may be provided on the fixing base, and the rotary driving rod may be connected with a rotor of the rotary encoder.

The rotary driving piece may be fixed to the connecting rod and has two ends provided with connecting holes, and the rotary driving piece may be connected with the rotary driving rod through the connecting holes.

The connecting rod may be able to drive the rotary driving piece to rotate, thereby driving the rotary encoder to rotate through the rotary driving rod.

Preferably, the rotary driving piece may be slidable on the rotary driving rod through the connecting holes.

Preferably, the operating handle further may include a thrust bearing, which has one end connected with the connecting rod and the other end connected with the strain gauge.

Preferably, the linear motor may transmit a moving distance and speed of the rotor of the linear motor to the main controller through a sensor.

Preferably, the sensor may include a grating ruler, a magnetic grating ruler, a distance meter, or a printed circuit board (PCB) distance sensor.

Compared with the prior art, the present disclosure has the following beneficial effects.

1. The operating handle of the present disclosure completely replicates the actual operation of the surgeon and can be operated by the surgeon only after a short period of learning.

2. The operating handle of the present disclosure can relay the contact force of the front-end guidewire/catheter during the advancing process in real time to the surgeon's hand in the form of resistance, so as to provide the surgeon with a better sense of presence.

3. The operating handle of the present disclosure has high control precision with a linear distance resolution of 7 μm, a rotation angle resolution of 0.08°, and a force feedback resolution of 0.5 g.

4. The operating handle of the present disclosure is composed of finished parts. The operating handle is practical and can be easily manufactured at low cost.

BRIEF DESCRIPTION OF THE DRAWINGS

Other features, objectives, and advantages of the present disclosure will become more apparent by reading the detailed description of non-limiting embodiments with reference to the following drawings.

REFERENCE NUMERALS

1. film-type strain gauge;
2. supporting sliding bearing;
3. rotary slip ring;
4. connecting rod;
5. rotary driving rod;
6. rotary driving piece;
7. rotary encoder;
8. fixing base;
9. bidirectional thrust bearing;
10. strain gauge;
11. linear motor;
12. sliding guide rail;
13. fixing base plate; and
14. operation rod.

DETAILED DESCRIPTION OF THE EMBODIMENTS

The present disclosure is described in detail below with reference to specific embodiments. The following embodiments will help those skilled in the art to further understand the present disclosure but do not limit the present disclosure in any way. It should be noted that several variations and improvements can also be made by a person of ordinary skill in the art without departing from the concept of the present disclosure. These all fall within the protection scope of the present disclosure.

Figure 1:
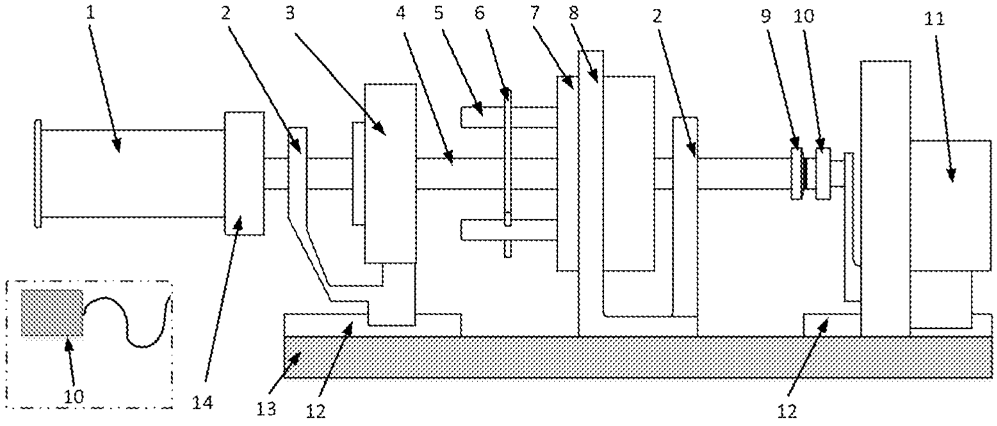
FIGS. 1 and 2 are structural views of an operating handle for a vascular intervention robot.
Figure 2:
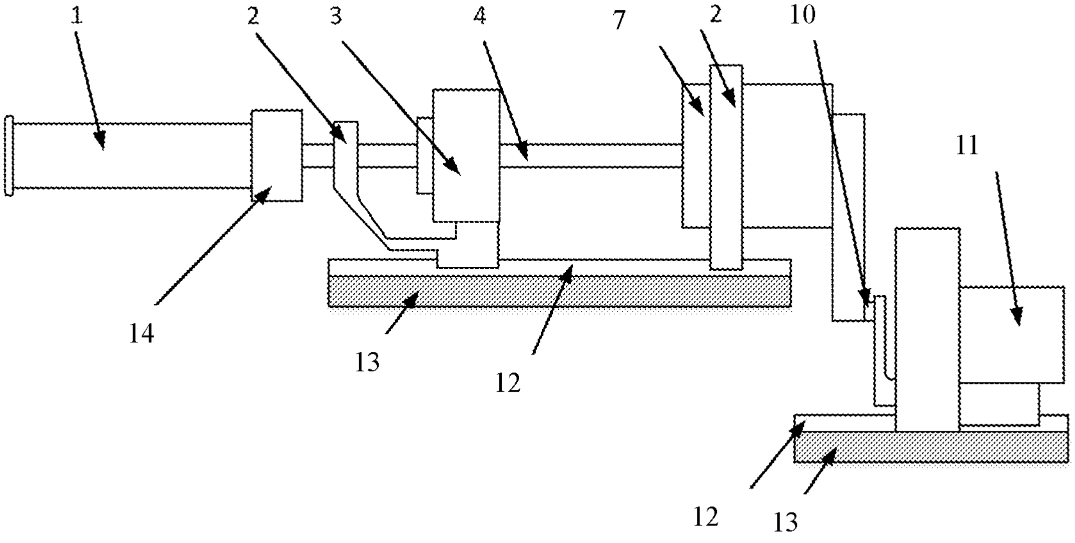
Figure 3:
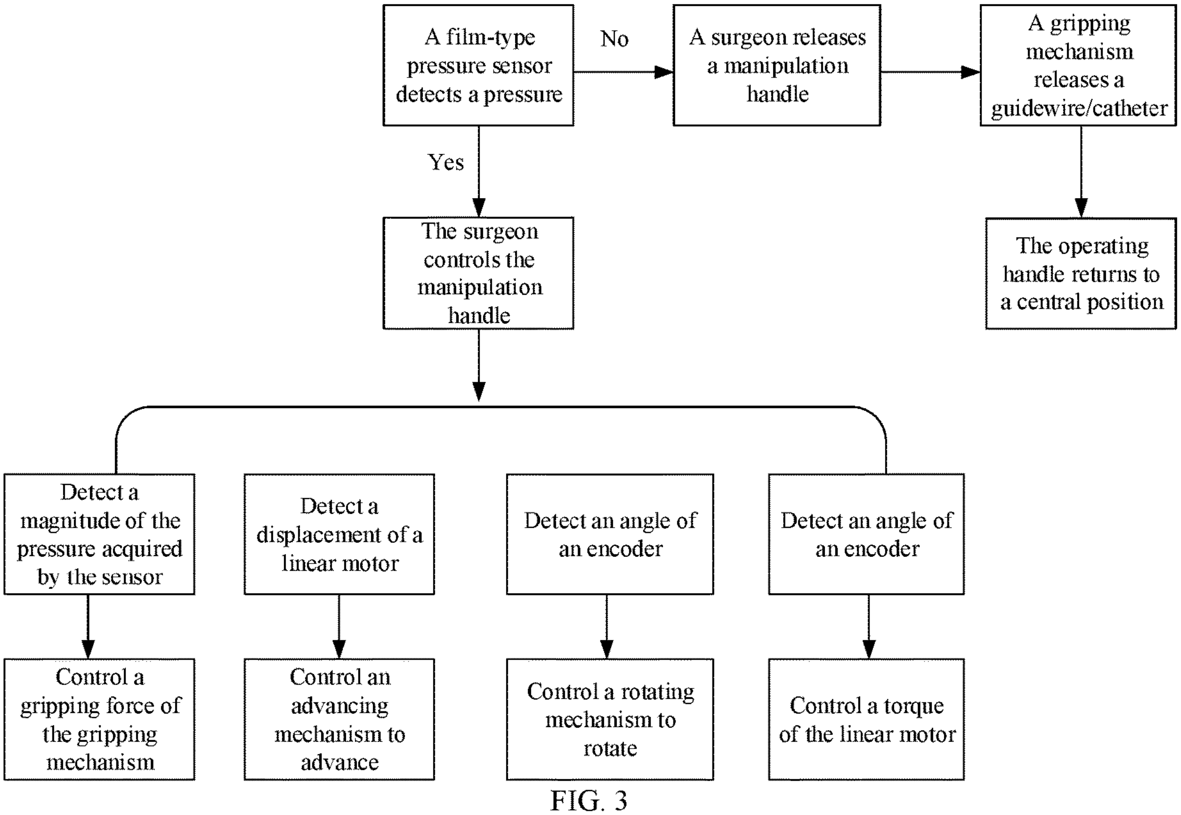
FIG. 3 is a control logic for force feedback of the operating handle.

As shown in FIGS. 1 to 3, the present disclosure provides an operating handle for a vascular intervention robot that provides feedback of guidewire/catheter advancement resistance. The operating handle simulates operation actions of a surgeon in vascular interventional surgery and replicates the actions of the surgeon to advance and rotate a guidewire/catheter, so as to control the front-end intervention robot to complete gripping, advancement, and rotation of the guidewire/catheter. Since the operation actions of the surgeon include several actions, the operating handle needs to decouple the operation actions of the surgeon. A force sensor and a power actuator relay the resistance encountered by the guidewire/catheter in the blood vessel during the advancement process to the operating handle. The operating handle then transmits the resistance to the surgeon to help the surgeon determine whether the guidewire/catheter is advanced smoothly during the interventional operation. The present disclosure replicates the operation actions of the surgeon in vascular interventional surgery through a two-degree-of-freedom (2-DoF) mechanism that performs linear and rotational motions. Specifically, the operating handle includes a film-type strain gauge 1, a supporting sliding bearing 2, a rotary slip ring 3, a connecting rod 4, a rotary driving rod 5, a rotary driving piece 6, a rotary encoder 7, a fixing base 8, a bidirectional thrust bearing 9, a strain gauge 10, a linear motor 11, a sliding guide rail 12, a fixing base plate 13, and an operation rod 14. The sliding guide rail 12, a stator of the linear motor 11 and the fixing base 8 are fixed on the fixing base plate 13. The rotary slip ring 3, a rotor of the linear motor 11, and the sliding bearing 2 are connected with the sliding guide rail 12 through a slider and are movable linearly along the sliding guide rail 12. The rotary encoder 7 is hollow and fixed to the fixing base plate through the fixing base 8. The operation rod 14, the rotary driving piece 6, the bidirectional thrust bearing 9, and the strain gauge 10 are connected with the connecting rod 4. The connecting rod 4 is supported by the supporting sliding bearing 2 and is slidable linearly and rotatable in the supporting sliding bearing 2. The film-type strain gauge 1 is attached to a surface of the operation rod 14. The rotary driving piece 6 is fixed to the connecting rod 4 and has two ends provided with holes. The rotary driving piece 6 is connected with the rotary driving rod 5 through the holes and is slidable on the rotary driving rod 5 through the holes. The rotary driving rod 5 is connected with a rotor of the rotary encoder. The bidirectional thrust bearing 9 has one end connected with the connecting rod 4 and the other end connected with the strain gauge 10. The connecting rod 4 is connected with the rotor of the linear motor 11 through the strain gauge 10. Another strain gauge 10 is provided in a guidewire/catheter advancing mechanism of the distal intervention robot for measuring an advancing force applied on the guidewire/catheter during the advancing process.

In a variation of the present disclosure, the operating handle includes a film-type strain gauge 1, a supporting sliding bearing 2, a rotary slip ring 3, a connecting rod 4, a rotary encoder 7, a strain gauge 10, a linear motor 11, a fixing base 8, and a sliding guide rail 12. The sliding guide rail 12, a stator of the linear motor 11, and the fixing base 2 are fixed on the fixing base plate 13. The rotary slip ring 3, the rotary encoder 7, a rotor of the linear motor 11, and the supporting sliding bearing 2 are connected with the sliding guide rail 12 through a slider and are movable linearly along the sliding guide rail 12. The operation rod 14 and the rotary encoder 7 are connected with the connecting rod 4. The connecting rod 4 is supported by the supporting sliding bearing 2 and a rotating end of the rotary encoder 7 and is linearly slidable and rotatable in the supporting sliding bearing 2. The film-type strain gauge 1 is attached to a surface of the operation rod 14. A fixed end of the rotary encoder 7 is connected with the rotor of the linear motor 11 through the strain gauge 10.

The working principle of the present disclosure is as follows:

In endovascular interventional surgery, the surgeon needs to perform three basic actions to manipulate the guidewire/catheter: the surgeon's fingers grip/release the guidewire/catheter, the surgeon's hand advances the guidewire/catheter linearly, and the surgeon's fingers rotate the guidewire/catheter.

I: Gripping/releasing action of the surgeon's fingers. The surgeon holds the operation rod 14 and controls a gripping force. The film-type pressure sensor 1 wrapped on the surface of the operation rod 14 converts the surgeon's gripping force into a current signal and transmits the current signal to a main controller through the rotary slip ring 3. The main controller identifies the surgeon's gripping action based on the current signal transmitted by the film-type pressure sensor 1. When the film-type pressure sensor 1 detects a pressure, it indicates that the surgeon is performing a gripping action. Thus, a gripping mechanism of the distal intervention robot is controlled to grip the guidewire/catheter. When the film-type pressure sensor 1 detects no pressure, it indicates that the surgeon is performing a releasing action. Thus, the gripping mechanism of the distal intervention robot is controlled to release the guidewire/catheter. The film-type pressure sensor 1 detects the magnitude of the surgeon's gripping force through a magnitude of an analog signal, thereby adjusting the magnitude of the gripping force of the gripping mechanism of the distal intervention robot.

II: Linear advancing action of the surgeon's hand. The surgeon controls the guidewire/catheter to advance linearly by linearly pulling or pushing the connecting rod 4 by the operation rod 14. The connecting rod 4 drives the rotor of the linear motor 11 to move through the bidirectional thrust bearing 9. A ruler (or a magnetic grating ruler, a distance meter, or a printed circuit board (PCB) distance sensor) of the linear motor 11 transmits a moving distance and speed of the rotor to the main controller. The moving distance and speed of the rotor reflect the pushing distance and speed of the surgeon's hand, and the distance and speed of the guidewire/catheter advanced by an advancing mechanism of the distal intervention robot are controlled based on the moving distance and speed of the rotor.

III: Rotating action of the surgeon. The surgeon rotates the connecting rod 4 by rotating the operation rod 14, thereby controlling the rotation of the guidewire/catheter. The rotation of the connecting rod 4 drives the rotary driving piece 6 to rotate, thereby driving the rotary driving rod 5 to rotate. The rotation of the rotary driving rod 5 drives the rotary encoder 7 to rotate. The rotary encoder acquires and transmits the angle and speed of the surgeon's rotating action to the main controller, so as to control the angle and speed of a rotating mechanism of the distal intervention robot to rotate the guidewire/catheter.

The advancing mechanism of the distal intervention robot is further provided therein with a strain gauge. The strain gauge detects the resistance of the guidewire/catheter during the advancing process, and transmits the resistance to the main controller in the form of an electrical signal. The main controller adjusts the current of the linear motor 11 according to the front-end resistance to generate a corresponding push or pull force until the current value acquired by the strain gauge 10 is equal to the current value measured by a front-end strain gauge. Since the surgeon is controlling the operation rod 14, the push/pull force of the linear motor is relayed to the surgeon through the connecting rod. As a result, the surgeon's hand experiences a resistance similar to that encountered in a real scenario of physically advancing the guidewire/catheter.

In the present disclosure, the linear motor 11 is configured to measure the operating displacement and transmit the resistance of the guidewire/catheter. The linear motor 11 measures the pushing distance of the surgeon by transmitting its position. The linear motor drives the operation rod to automatically return to a central position through its position control mode and relays the advancing force to the surgeon through its torque control mode. The present disclosure solves the problems that the multi-DoF motion of the decoupling mechanism of the rotary slip ring 3, the crank-like rocker mechanism, and the direct thrust bearing (or magnet) conflicts with the single-DoF motion of a single component and that the cords may become tangled. The present disclosure decouples the movement of the gripping force sensor and the restraint of the fixed cord through the hollow rotary slip ring 3. The gripping force sensor is fixedly connected with the operation rod and is movable linearly and rotationally with the operation rod, and the lead wires of the gripping force sensor are also movable with the operation rod. The present disclosure solves the problem of cord tangling by decoupling the rotational motion and the linear motion through the hollow rotary slip ring 3. The present disclosure decouples the movement of the operation rod and the rotational movement of the rotary encoder 7 through the sliding bearing and the crank structure. The connecting rod 4, the rotary driving piece 6 and the rotary driving rod 5 form the crank structure, which can measure the rotation angle and speed of the connecting rod 4 without disturbing the linear motion of the connecting rod 4. The present disclosure decouples the rotational motion of the operation rod and the linear motion of the linear motor 11 through the bidirectional thrust bearing 9 or a magnet. The connecting rod 4 can perform linear motion and rotational motion, that is, 2-DOF motion, while the linear motor 11 can only perform linear motion. Therefore, the present disclosure decouples the 2-DOF motion of the connecting rod 4 and the single-DOF motion of the linear motor 11 through the bidirectional thrust bearing 9 or the magnet.

The specific embodiments of the present disclosure are described above. It should be understood that the present disclosure is not limited to the above specific implementations, and a person skilled in the art can make variations or modifications within the scope of the claims without affecting the essence of the present disclosure. The embodiments in the present disclosure and features in the embodiments may be combined with each other in a non-conflicting situation.

What is claimed is:

1. An operating handle with a feedback of guidewire/catheter advancement resistance for a vascular intervention robot comprising a sliding guide rail, a fixing base plate, a connecting rod, an operation rod, a pressure sensing device, a rotary driving device, and a linear motor, wherein the rotary driving device, the sliding guide rail, and a stator of the linear motor are arranged on the fixing base plate;

the pressure sensing device and a rotor of the linear motor are connected with the sliding guide rail through a slider and are configured to reciprocate along the sliding guide rail;

the connecting rod has a first end provided with the operation rod and a second end connected with the rotor of the linear motor through a strain gauge; and the connecting rod passes through the pressure sensing device and the rotary driving device in sequence;

wherein the rotary driving device comprises a fixing base, a rotary encoder, a rotary driving piece, and a rotary driving rod, the rotary encoder is provided on the fixing base; and the rotary driving rod is connected with a rotor of the rotary encoder;

the rotary driving piece is fixed to the connecting rod and has two ends provided with connecting holes; and the rotary driving piece is connected with the rotary driving rod through the connecting holes; and the connecting rod is configured to drive the rotary driving piece to rotate so as to drive the rotary encoder to rotate through the rotary driving rod.

2. The operating handle according to claim 1, wherein the pressure sensing device comprises a film-type pressure sensor, a first sliding bearing, and a rotary slip ring, the film-type pressure sensor is wrapped on a surface of the operation rod;

the first sliding bearing and the rotary slip ring are arranged on the sliding guide rail; and the film-type pressure sensor is electrically connected with the rotary slip ring, and the rotary slip ring is externally connected with a main controller.

3. The operating handle according to claim 2, further comprising a second sliding bearing, the second sliding bearing is fixed to the fixing base plate, and the first sliding bearing and the second sliding bearing support the connecting rod.

4. The operating handle according to claim 1, wherein the rotary driving piece is slidable on the rotary driving rod through the connecting holes.

5. The operating handle according to claim 1, further comprising a thrust bearing, wherein a first end of the thrust bearing is connected with the connecting rod and a second end of the thrust bearing is connected with the strain gauge.

6. The operating handle according to claim 1, wherein the linear motor is configured to transmit a moving distance and speed of the rotor of the linear motor to a main controller through a sensor.

7. The operating handle according to claim 6, wherein the sensor comprises a grating ruler, a magnetic grating ruler, a distance meter, or a printed circuit board (PCB) distance sensor.

* * * * *